United States Patent [19]

Tully et al.

[11] Patent Number: 4,472,400
[45] Date of Patent: Sep. 18, 1984

[54] TRIAZOLOQUINAZOLONES HAVING ANTIHISTAMINIC AND BRONCHOSPASMOLYTIC ACTIVITY

[75] Inventors: Wilfred R. Tully, Cirencester; Robert Westwood, Faringdon; David A. Rowlands, Malmesbury; Stephen Clements-Jewery, Near Swindon, all of England

[73] Assignee: Roussel Uclaf, Paris, France

[21] Appl. No.: 420,798

[22] Filed: Sep. 21, 1982

[30] Foreign Application Priority Data

Sep. 24, 1981 [GB] United Kingdom ............... 8128875

[51] Int. Cl.³ .................. A61K 31/505; C07D 487/04
[52] U.S. Cl. .................................. 424/251; 424/246;
424/248.57; 260/243.3; 544/60; 544/115;
544/251
[58] Field of Search .................. 544/251, 115, 60;
424/251, 248.57, 246; 260/243.3

[56] References Cited

U.S. PATENT DOCUMENTS

| 4,002,755 | 1/1977 | Yamamoto et al. | 544/251 |
|---|---|---|---|
| 4,145,419 | 3/1979 | Rolands et al. | 424/248.4 |
| 4,151,280 | 4/1979 | Rowlands et al. | 424/250 |
| 4,207,318 | 6/1980 | Rolands et al. | 424/248.4 |
| 4,254,123 | 3/1981 | Ramm et al. | 424/250 |
| 4,279,912 | 7/1981 | Ager et al. | 424/258 |
| 4,291,033 | 9/1981 | Barnes et al. | 424/250 |
| 4,333,934 | 6/1982 | Barnes et al. | 424/250 |

FOREIGN PATENT DOCUMENTS 0139715  1/1980  German Democratic Rep. .................................. 424/251

OTHER PUBLICATIONS

Kottke, et al., Chemical Abstracts, vol. 89, 129470v, (1978).
Renner, et al., Chemical Abstracts, vol. 94, No. 17, 132238j, (04/27/81).

Primary Examiner—Donald G. Daus
Assistant Examiner—Diana G. Rivers
Attorney, Agent, or Firm—Charles A. Muserlian

[57] ABSTRACT

Novel triazoloquinazolones of the formula

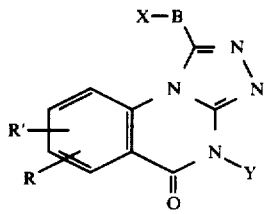

wherein R and R' are individually selected from the group consisting of hydrogen, halogen, nitro and alkyl and alkoxy of 1 to 3 carbon atoms, Y is selected from the group consisting of alkyl of 1 to 6 carbon atoms, alkenyl of 2 to 4 carbon atoms, cycloalkyl of 3 to 8 carbon atoms, aryl of 6 to 8 carbon atoms and aralkyl of 7 to 8 carbon atoms, B is an alkylene of 1 to 3 carbon atoms, X is selected from the group consisting of

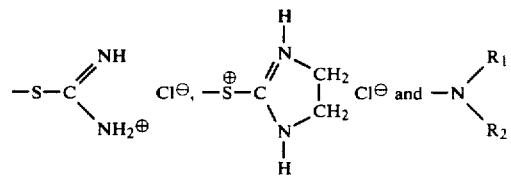

$R_1$ and $R_2$ are individually selected from the group consisting of hydrogen, alkyl of 1 to 6 carbon atoms, cycloalkyl of 3 to 8 carbon atoms, aryl of 6 to 8 carbon atoms, aralkyl of 7 to 8 carbon atoms, aminoalkyl of 2 to 4 carbon atoms, mono- and dialkylaminoalkyl with each alkyl having 2 to 4 carbon atoms, piperidinoalkyl of 1 to 4 alkyl carbon atoms, morpholinoalkyl of 1 to 4 alkyl carbon atoms and piperazinylalkyl of 1 to 4 alkyl carbon atoms or $R_1$ and $R_2$ taken together with the nitrogen to which they are attached form a saturated mono- or bicyclic heterocyclic ring with 4 to 8 carbon atoms optionally substituted with 1 to 2 methyls and optionally containing in the ring a heteroatom selected from —O—, —S— and

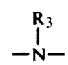

and $R_3$ is selected from the group consisting of hydrogen, alkyl of 1 to 3 carbon atoms, hydroxyalkyl of 1 to 3 carbon atoms, alkoxycarbonyl of 2 to 5 carbon atoms, aryl of 6 to 8 carbon atoms and aralkyl of 7 to 8 carbon atoms and their non-toxic, pharmaceutically acceptable acid addition salts having antihistaminic and bronchospasmolytic activity and their preparation and intermediates.

16 Claims, No Drawings

TRIAZOLOQUINAZOLONES HAVING ANTIHISTAMINIC AND BRONCHOSPASMOLYTIC ACTIVITY

STATE OF THE ART

Commonly assigned U.S. Pat. No. 4,145,419, No. 4,279,912, No. 4,151,280, No. 4,207,318, No. 4,291,033, No. 4,254,123 and No. 4,333,934 disclose various triazoloquinazolones of different structures.

OBJECTS OF THE INVENTION

It is an object of the invention to provide the novel triazoloquinazolones of formula I and their non-toxic, pharmaceutically acceptable acid addition salts and a novel process and novel intermediates for their preparation.

It is another object of the invention to provide novel antihistaminic and bronchospasmolytic compositions and to a novel method of inducing antihistaminic and bronchospasmolytic activity in warm-blooded animals.

These and other objects and advantages of the invention will become obvious from the following detailed description.

THE INVENTION

The novel compounds of the invention are selected from the group consisting of triazoloquinazolones of the formula

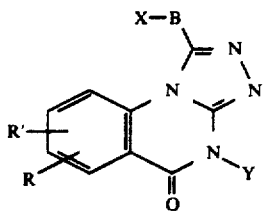

wherein R and R' are individually selected from the group consisting of hydrogen, halogen, nitro and alkyl and alkoxy of 1 to 3 carbon atoms, Y is selected from the group consisting of alkyl of 1 to 6 carbon atoms, alkenyl of 2 to 4 carbon atoms, cycloalkyl of 3 to 8 carbon atoms, aryl of 6 to 8 carbon atoms and aralkyl of 7 to 8 carbon atoms, B is an alkylene of 1 to 3 carbon atoms, X is selected from the group consisting of

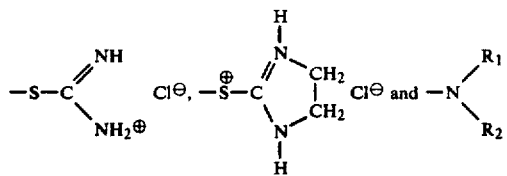

$R_1$ and $R_2$ are individually selected from the group consisting of hydrogen, alkyl of 1 to 6 carbon atoms, cycloalkyl of 3 to 8 carbon atoms, aryl of 6 to 8 carbon atoms, aralkyl of 7 to 8 carbon atoms, aminoalkyl of 2 to 4 carbon atoms, mono- and dialkylaminoalkyl with each alkyl having 2 to 4 carbon atoms, piperidinoalkyl of 1 to 4 alkyl carbon atoms, morpholinoalkyl of 1 to 4 alkyl carbon atoms and piperazinylalkyl of 1 to 4 alkyl carbon atoms or $R_1$ and $R_2$ taken together with the nitrogen to which they are attached form a saturated mono- or bicyclic heterocyclic ring with 4 to 8 carbon atoms optionally substituted with 1 to 2 methyls and optionally containing in the ring a heteroatom selected from —O—, —S— and

and $R_3$ is selected from the group consisting of hydrogen, alkyl of 1 to 3 carbon atoms, hydroxyalkyl of 1 to 3 carbon atoms, alkoxycarbonyl of 2 to 5 carbon atoms, aryl of 6 to 8 carbon atoms and aralkyl of 7 to 8 carbon atoms and their non-toxic, pharmaceutically acceptable acid addition salts.

Examples of R and R' are halogen such as fluorine, bromine and preferably chlorine and alkyl of 1 to 6 carbon atoms in formula I may be methyl, ethyl, n-propyl, isopropyl, butyl, isobutyl, tert.-butyl, pentyl and hexyl and aryl and aralkyl may be phenyl, benzyl or phenethyl. Y, $R_1$ and/or $R_2$ may also be cycloalkyl of 3 to 8 carbon atoms such as cyclopropyl, cyclopentyl and cyclohexyl and Y may be alkenyl of 2 to 4 carbon atoms such as vinyl or allyl.

Examples of $R_1$ and/or $R_2$ are aminoalkyl or mono- or dialkylaminoalkyl with alkyls of 2 to 4 carbon atoms are aminoethyl, methylaminoethyl and dimethylaminoethyl and as piperidinoalkyl, morpholinoalkyl and piperazinylalkyl are piperidinoethyl, morpholinoethyl and piperazinylethyl.

Examples of $R_1$ and $R_2$ taken together with the nitrogen forming saturated mono- and bicyclic heterocyclic groups are pyrrolidinyl, piperidino, 2,3,4,5,6,7-hexahydro-azepino, 3-azabicyclo [3,2,2]nonano, 2,6-dimethylpiperidino, 3,5-dimethylpiperidino, morpholino, thiomorpholino and piperazin-1-yl.

Examples of suitable acids for the formation of the non-toxic, pharmaceutically acceptable acid addition salts are inorganic acids such as hydrochloric acid, hydrobromic acid, hydroiodic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkanesulfonic acids such as methanesulfonic acid and arylsulfonic acids such as benzene sulfonic acid.

Preferred compounds of formula I are those wherein R and R' are individually hydrogen, chlorine, methyl, methoxy or nitro, those wherein Y is alkyl of 1 to 6 carbon atoms, cyclohexyl, allyl, phenyl or benzyl and those wherein B is —CH₂— or —CH₂—CH₂— and their non-toxic, pharmaceutically acceptable acid addition salts.

Especially preferred compounds of formula I are those wherein R and R' are hydrogen, Y is methyl, ethyl, n-propyl, isopropyl, n-butyl, tert.-butyl, n-hexyl, cyclohexyl, allyl, phenyl or benzyl and X is amino, dimethylamino, diethylamino, dipropylamino, diisopropylamino, dibutylamino, diisobutylamino, butylamino, cyclohexylamino, piperidinoethylamino, pyrrolidinyl, piperidino, 2,3,4,5,6,7-hexahydroazepino, 3-azabicyclo[3,2,2]nonano, 2,6-dimethylpiperidino, 3,5-dimethylpiperidino, morpholino,piperazin-l-yl, methylpiperazin-1-yl, hydroxyethylpiperazin-1-yl, phenylpiperazin-1-yl or ethoxycarbonylpiperazin-1-yl and their non-toxic, pharmaceutically acceptable acid addition salts. Of these more preferred compounds, especially preferred are those wherein B is methylene and X is pyrrolidinyl, piperidino, 2,3,4,5,6,7-hexahydroazepino, 3-azabicyclo[3,2,2]nonano, 2,6-dimethylpiperidino or 3,5-dimethylpiperidino and their non-toxic, pharmaceutically acceptable acid addition salts.

Specific preferred compounds of formula I are 1-piperidinomethyl-4-ethyl[1,2,4]triazolo[4,3-a]quinazolin-5 (4H)-one, 1-piperidinomethyl-4-n-propyl[1,2,4]-triazolo[4,3-a] quinazolin-5(4H)-one, 1-piperidinomethyl-4-isopropyl[1,2,4] triazolo[4,3-a]quinazolin-5(4H)-one, 1-piperidinomethyl-4-n-butyl[1,2,4]-triazolo[4,3-a]quinazolin-5(4H)-one, 1-(2,3,4,5,6,7,-hexahydroazepino)methyl-4-n-butyl[1,2,4]triazolo[4,3-a]quinazolin-5(4H)-one, 1-piperidinomethyl-4-allyl[1,2,4]triazolo[4,3-a]quinazolin-5(4H)-one and their non-toxic, pharmaceutically acceptable acid addition salts.

The process of the invention for the preparation of the compounds of formula I comprises reacting a compound of the formula

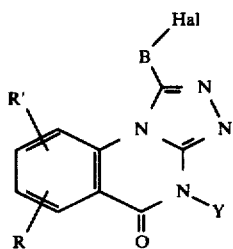  II wherein R, R', Y and B have the above definitions and Hal is chlorine or bromine with a compound of the formula

 III wherein X has the above definition.

The reaction is conveniently effected in the presence of an organic solvent such as toluene and optionally in the presence of an alkaline agent.

The compounds of formula II are novel compounds and are an object of the invention and may be prepared by reacting a compound of the formula

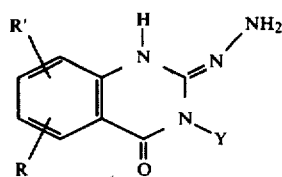 IV wherein R, R' and Y have the above definitions with a compound of the formula

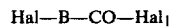 V wherein B and Hal have the above definitions and Hal₁ is bromine or preferably chlorine. In the compound of formula V, Hal is preferably chlorine and the reaction is conveniently effected in the presence of an organic solvent such as dimethylformamide and optionally in the presence of an alkaline agent.

According to a modification of the above method, compounds of formula II may be obtained by cyclizing a compound of the formula

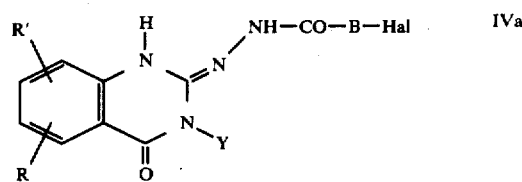 IVa wherein R, R', Y, B and Hal have the above definitions. Cyclization may conveniently be effected by heating the compound of formula IVa in the presence of an acid such as e.g. p-toluene sulfonic acid. The compound of formula IVa may itself be prepared, for example, by reaction of a compound of formula IV as hereinbefore defined with a compound of formula V as hereinbefore defined whereby the desired compound of formula IVa may be isolated. Thus, compounds of formula II may be obtained from the corresponding compound of formula IV either directly or with isolation of the intermediate of formula IVa.

Compounds of formula I wherein Y is alkyl of 2 to 4 carbon atoms may also conveniently be prepared by hydrogenation of a corresponding compound of formula I wherein Y is alkenyl of 2 to 4 carbon atoms, for example with hydrogen in the presence of a catalyst such as e.g. palladium.

The compounds of formula I may, if desired, be converted into their acid addition salts by reaction with an acid, preferably in equimolar amounts.

The compounds of formula IV, when they are not known, may be prepared by reaction of an acid of the formula

 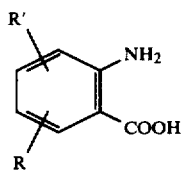 VI wherein R and R' have the above definitions or an ester thereof e.g. a lower alkyl ester with a compound of the formula

 Y—N=C=S VII wherein Y has the above definition to give a compound of the formula

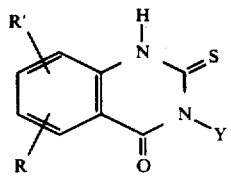 VIII wherein R, R' and Y have the above definitions which is then reacted with hydrazine hydrate to give the desired compound of formula IV.

A number of the compounds of formula VIII are known. Thus compounds of formula VIII wherein R and R' each is hydrogen and Y is methyl, ethyl or benzyl are described in C.A., Vol. 70,11671 r. and compounds of formula VIII wherein R and R' each is hydrogen and Y is allyl or phenyl are described in C.A., Vol. 61, 8307 g. The remaining compounds of formula VIII may be obtained by analogous methods.

A number of the compounds of formula IV are also known. Thus, for example, the compounds of formula IV wherein R and R' each is hydrogen and Y is methyl are described in C.A., Vol. 85, 5681 n. Compounds of formula IV wherein R and R' each is hydrogen and Y is allyl or phenyl have also been described.

Certain of the compounds of formula IV and especially those wherein Y is alkyl of 1 to 6 carbon atoms, when they are not known, may be prepared by reacting a compound of the formula

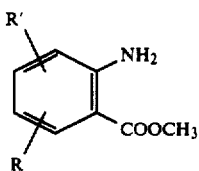

wherein R and R' have the above definitions with a compound of the formula

wherein Y has the above definition to obtain a compound of the formula

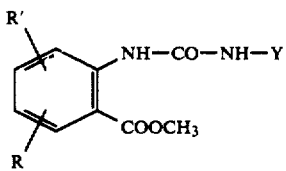

wherein R, R' and Y have the above definitions which compound is then cyclized by heating in the presence of an acid to give a compound of the formula

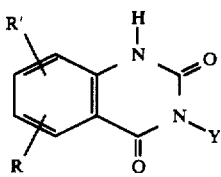

wherein R, R' and Y have the above definitions and reacting the said compound of formula XII with phosphorus oxychloride to obtain a compound of the formula

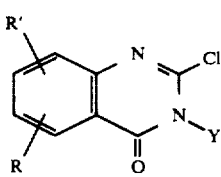

wherein R, R' and Y have the above definitions and reacting the latter with hydrazine hydrate to give the desired compound of formula IV.

Some of the compounds of formula XI are known. Thus, for example, compounds of formula XI wherein R and R' each is hydrogen and Y is n-propyl or n-butyl are described in C.A., Vol. 56, 14283b. Certain of the compounds of formula XII are also known. Thus, for example, compounds of formula XII wherein R and R' each is hydrogen and Y is n-propyl-or n-butyl are described in C.A., Vol. 56, 14283b and those wherein R and R' each is hydrogen and Y is isopropyl are described in C.A., Vol. 70, 4141q.

The preparation of intermediates of formula IV is illustrated hereinafter in the Examples.

The novel antihistamic and bronchospasmolytic compositions of the invention are comprised of an antihistaminically and bronchospasmolytically effective amount of at least one compound of formula I and their non-toxic, pharmaceutically acceptable acid addition salts and an inert pharmaceutical carrier or excipient. The compositions may be in the form of tablets, dragees, gelatin capsules, granules, aerosols, suppositories and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various propellant, wetting, dispersing or emulsifying agents and/or preservatives.

Advantageously, the compositions may be formulated as dosage units, each unit being adapted to supply a fixed dose of active ingredient. Suitable dosage units for adults contain from 2 mg to 2 g, preferably from 2 mg to 1 g of active ingredient. The oral daily dosage, which may be varied according to the compound used, the subject treated and the complaint concerned, may, for example, be from 2 mg to 2 g per day in adults.

The compositions are useful for the treatment of asthma, bronchitis and allergic disorders.

The novel method of the invention for inducing antihistaminic and bronchospasmolytic activity in warm-blooded animals, including humans, comprises administering to warm-blooded animals an antihistaminically and bronchospasmolytically effective amount of at least one compound of formula I and their non-toxic, pharmaceutically effective addition salts. The compounds may be administered orally, rectally or parenterally and the daily dose is 0.03 to 30 mg/kg depending on the specific compound, the condition being treated and the administration method.

In the following examples there are described several preferred embodiments to illustrate the invention. However, it is to be understood that the invention is not intended to be limited to the specific embodiments.

EXAMPLE 1

1-Piperidinomethyl-4-n-propyl[1,2,4]triazolo[4,3-a]quinazolin-5(4H)-one hydrochloride, monohydrate

STEP A: Methyl N-(N'-n-propylcarbamoyl)-anthranilate

A mixture of 159 g of methyl anthranilate (1.053 mole), 5 ml of triethylamine and 134 g of n-propylisocyanate (1.58 mole) in 700 ml of petroleum ether (60°-80° C.) was refluxed for seventeen hours until TLC ($CH_2Cl_2$, silica) indicated that no methyl antranilate remained. The mixture was cooled and the precipitate was filtered off, washed with a little cold petroleum ether and dried under vacuum at room temperature to obtain 236 g (95% yield) of methyl N-(N'-n-propylcarbamoyl)-anthranilate melting at 101.5°-102.5° C.

STEP B: 3-n-Propylquinazoline-2,4(1H,3H)-dione

A mixture of 232 g of methyl N-(N'n-propylcarbamoyl)-anthranile (0.983 mole) and 750 ml of concentrated hydrochloric acid in 1 liter of ethanol was refluxed for three hours until TLC ($CH_2Cl_2$+5% MeOH, silica) indicated that no starting material remained. The mixture was then cooled and then product crystallized out. The product was filtered, washed with ether and dried under vacuum to obtain 186 g (93% yield) of 3-n-propylquinazoline-2,4(1H,3H)-dione melting at 188°–188.5° C.

STEP C: 2-Chloro-3-n-propylquinazolin-4(3H)-one 181 g of 3-n-propylquinazoline-2,4-(1H,3H)-dione (0.887 mole) in 1200 ml of phosphorus oxychloride was refluxed for two days when TLC ($SiO_2$, $CH_2Cl_2$/2% MeOH) indicated that most of the starting material had gone. TLC was carried out by pipetting a small portion of the reaction mixture into ice-water, allowing the hydrolysis of $POCl_3$ to occur at 0° C. for 15 min. and then extracting the cold solution with chloroform. The TLC plate when run might be expected to show a small amount of starting dione derived from hydrolysis of the imino chloride during the work up-TLC procedure.

Most of the excess $POCl_3$ was then evaporated under reduced pressure while keeping the temperature below 50° C. and the remaining 400 ml of the mixture were poured carefully into 4 kg of ice-water with stirring. After keeping the mixture at 0° C. for 30 minutes to allow hydrolysis of the $POCl_3$ to occur, the mixture was extracted twice at about 0° C. with chloroform and the chloroform solution was dried over $MgSO_4$, filtered and evaporated to dryness to give a crude 2-chloro-3-n-propylquinolin-4(3H)-one which was used without further purification.

STEP D: 2-Hydrazino-3-n-propylquinazolin-4(3H)-one

The crude solid imino chloride of Step C was dissolved in 800 ml of ethanol and 400 ml of hydrazine hydrate and the mixture was refluxed for two hours until TLC indicated ($SiO_2$, $CH_2Cl_2$/2% MeOH) that no imino chloride remained. 500 ml of water were added to the mixture and the mixture was cooled inducing a crystalline precipitate of the product. The precipitation was filtered, washed well with water, then dried over $P_2O_5$ under vacuum to obtain 158 g (82% yield) of 2-hydrazino-3-n-propylquinazolin-4(3H)-one in the form of a pale yellow solid melting at 125°–8° C.

IR Spectrum 761, 1448, 1482, 1568, 1583, 1680, 3320 cm$^{-1}$.

STEP E: 1-Chloromethyl-4-n-propyl[1,2,4]triazolo[4,3-a]-quinazolin-5(4H)-one 156 g of 2-hydrazino-3-n-propylquinazolin-4(3H)-one (0.72 mole) were suspended in 500 ml of dimethylformamide and 90 g of chloroacetyl chloride (0.80 mole) were added in portions with cooling in an ice bath. When the addition was complete, the mixture was heated on a hot water bath for three hours until TLC ($SiO_2$ EtOAc) indicated no starting material or intermediate remaining. The resultant mixture was poured into one liter of water and one liter of ethyl acetate and 500 ml of dichloromethane and the organic and aqueous layers were separated. The aqueous layer was extracted twice more with 500 ml of ethyl acetate and the combined organic layers were extracted twice with 500 ml of water, dried over $MgSO_4$, filtered and evaporated to dryness. The crystalline residue was triturated with ether, filtered, washed with ether and dried under vacuum over $P_2O_5$ to obtain 146 g (74% yield) of the 1-chloromethyl-4-n-propyl[1,2,4]triazolo[4,3-a]-quinazolin-5(4H)-one melting at (capillary) 141°–145° C.

STEP F: 1-Piperidinomethyl-4-n-propyl[1,2,4]triazolo[4,3-a] quinazolin-5(4H)-one, hydrochloride salt, monohydrate 111 g of 1-chloromethyl-4-n-propyl[1,2,4]triazolo [4,3-a]quinazolin-5-(4H)-one (0.40 mole) were suspended in 500 ml of toluene and 73.6 g of piperidine (0.87 mole) were added thereto. The mixture was refluxed for two hours and TLC ($SiO_2$, EtOAc) then indicated no starting material remaining. The mixture was poured into 1 liter of water and one liter of ethyl acetate and shaken. After separation of the layers, the aqueous layer was twice extracted with 250 ml of ethyl acetate and the combined organic layers were washed once with 500 ml of water, dried over $MgSO_4$, filtered and evaporated to dryness. A crystalline product was obtained which was triturated with ether, filtered, washed well with ether, dried under vacuum over $P_2O_5$ to obtain 108.6 g of free base and a second crop of 4.5 g for a total yield of 86.5% melting at (capillary) 160°–66° C.

11 g of the free base were dissolved in 500 ml of hot ethanol and HCl/$Et_2O$ was added followed by ether. The salt crystallized out on scratching and was filtered and dried under vacuum to obtain 84.4 g of product. A second crop of 20 g was obtained from the mother liquors, and the combined crop (104.4 g) was crystallized from hot methanol to which ether was added. The crystalline product was filtered, washed well with ether and dried under vacuum. It was found necessary to dry the salt at 70° C. under vacuum to remove all traces of methanol and then on standing, the dried salt took up water from the atmosphere until 1-piperidinomethyl-4-n-propyl[1,2, 4]triazolo[4,3-a]quinazolin-5(4H)-one, hydrochloride salt, monohydrate was formed. The final weight of 100.6 g, (77.5% yield) melting at (capillary) 210°–16° C.

EXAMPLE A

Using a method similar to that used in the preparation of 2-hydrazino-3-n-propylquinazolin-4(3H)-one but starting from the corresponding compound of formula IX, a yield of 57% of 2-hydrazino-3-isopropylquinazolin-4(3H)-one was obtained which melted at 123°–124° C.

IR Spectrum

Absorption at 775, 1315, 1370, 1480, 1585, 1680, 3320 cm$^{-1}$

EXAMPLE B

Using a method similar to that used in the preparation of 2-hydrazino-3-n-propylquinazolin-4(3H)-one but starting from the corresponding compound of formula IX, a 33% yield of 3-n-butyl-2-hydrazinoquinazolin-4(3H)-one was obtained.

IR Spectrum

Absorption at 770, 1060, 1140, 1480, 1570, 1590, 1680, 3290 cm$^{-1}$.

EXAMPLE C

3-Benzyl-2-hydrazinoquinazolin-4(3H)-one starting from compound of formula IV in Example 32 (method b)

STEP A: 3-Benzyl-2-thioquinazoline-2,4(1H,3H)-dione 22.5 g of anthranilic acid (0.165 mole) were suspended in 300 ml of absolute ethanol and 25 g of benzyl isothiocyanate (0.168 mole) were added thereto. The mixture was refluxed for four hours, then cooled and filtered to obtain, after washing well with ether and drying under vacuum over $P_2O_5$, 13.7 g of 3-benzyl-2-thioquinazoline-2,4(1H,3H)dione melting at (capillary) 253°-4° C. which was a 31% yield.

STEP B: 3-Benzyl-2-hydrazinoquinazolin-4(3H)-one 13.3 g of 3-benzyl-2-thioquinazoline-2,4(1H,3H)-dione (0.05 mole) were suspended in 160 ml of ethanol and 10 ml of hydrazine hydrate were added thereto. The mixture was refluxed for three hours during which time the product crystallized out. The product was filtered, washed with a little alcohol and ether and dried to obtain 8.4 g of 3-benzyl-2-hydrazinoquinolin-4(3H)-one. A second crop was obtained by further heating of the mother liquors followed by evaporation of the ethanol solution which was filtered. The product was dried to obtain another 1.25 g of product for a total yield of 9.65 g (71% yield) melting at 156°-158° C.

IR Spectrum

Absorption at 1286, 1450, 1477, 1520–1610, 1688 and 2300-3700 cm$^{-1}$.

EXAMPLE D

Using a method similar to that used in the preparation of 3-benzl-2-hydrazinoquinazolin-4(3H)-one but starting from the corresponding compound of formula VI, 3-ethyl-2-hydrazinoquinazolin-4(3H)-one was obtained.

EXAMPLES 2 to 42

STEP A

Using a method similar to that used in Step E of Example 1 and starting from the corresponding compound of formula IV, the following compounds of formula II in which Hal is chlorine were prepared as indicated in Table II below. In the following Tables II and III, "method a" indicates that the corresponding compound of formula IV was prepared from a compound of formula IX as described in Steps A to D of Example 1 and "method b" indicates that the corresponding compound of formula IV was prepared from a compound of formula VI as described in Example C.

4-allyl-1-(2-chloroethyl)[1,2,4]triazolo[4,3-a]quinazolin-5(4H)-one prepared in Step A of Example 35 was also prepared as indicated below, this being referred to in Table II as "method d".

STEP A:
3-allyl-2-(2-(3-chloropropionyl)hydrazino)quinazoline-4(3H)-one

To a stirred mixture of 4.50 g of 3-allyl-2-hydrazino-quinazolin-4(3H)-one (0.0208 mol) and 5.75 g of anhydrous potassium carbonate (0.0416 mol; 2 eq) in 100 ml of chloroform at room temperature as added 2.2 ml of 3-chloropropionyl chloride (2.91 g; 0.023 mol; 1.1 eq). Almost immediately, a precipitate appeared and after 1 hr, 50 ml of water were added to the stirred mixture to dissolve any potassium carbonate. The mixture was filtered and the product was washed twice with water then twice with ether, crystallized from ethanol and dried under vacuum over $P_2O_5$ at 80° C. to obtain 5.79 g (91% yield) of 3-allyl-2-(2-(3-chloropropionyl)hydrazino)quinazolin-4(3H)-one melting at 151°-153° C.

STEP B: 4-allyl-1-(2-chloroethyl)[1,2,4]triazolo[4,3-a]quinazolin-5(4H)-one

A mixture of 5.30 g of 3-allyl-2-[2-(3-chloropropionyl)hydrazino]quinazolin-4(3H)-one (0.0173 mol) and 10 mg of p-toluenesulfonic acid hydrate in 300 ml of ethanol was refluxed for 17 hours until TLC indicated that no starting material remained. The mixture was evaporated to dryness and the remaining yellow oil was dissolved in dichloromethane. The solution was washed twice with water, dried over $MgSO_4$, filtered and evaporated. The resulting solid was purified by column chromatography using Kieselgel 60 with $CH_2Cl_2 + 1\%$ MeOH as eluant and then was finally crystallized from ethanol to obtain 2.625 g (53% yield) of 4-allyl-1-(2-chloroethyl)[1,2,4]triazolo[4,3-a]quinazolin-5(4H)-one melting at 142.5°-144° C.

TABLE II

| Ex | R | R' | B | Y | method | Yield % | Recrystallised Solvent | IR cm$^{-1}$ |
|---|---|---|---|---|---|---|---|---|
| 1-18 | H | H | CH$_2$ | —(CH$_2$)$_2$—CH$_3$ | a | 74 | EtOAc | 756, 1497, 1569, 1618, 1686 |
| 19-20 | H | H | CH$_2$ | —CH(CH$_3$)CH$_3$ | a | 65 | EtOAc | 765, 1275, 1460, 1500, 1570, 1610, 1623, 1695 |
| 21-22 | H | H | CH$_2$ | —(CH$_2$)$_3$—CH$_3$ | b | 67 | EtOAc | 760, 1300, 1500, 1570, 1605, 1620, 1695 |

TABLE II-continued

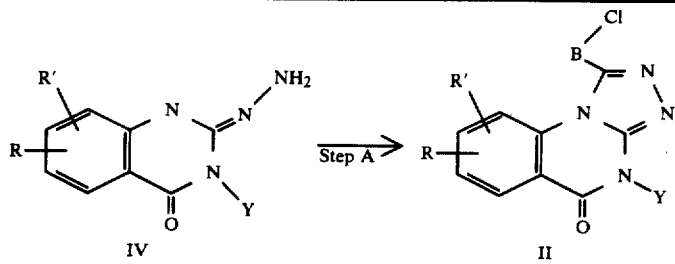

| Ex | R | R' | B | Y | method | Yield % | Recrystallised Solvent | IR cm$^{-1}$ |
|---|---|---|---|---|---|---|---|---|
| 23-28, 36, 37 | H | H | CH$_2$ | —CH$_3$ | b | 52 | EtOAc/CHCl$_3$ | 760, 1500, 1567, 1603, 1621, 1682 |
| 29-30 | H | H | CH$_2$ | —C$_2$H$_5$ | b | 78 | EtOAc | |
| 31 | H | H | CH$_2$ | phenyl | b | 43 | EtOAc/Et$_2$O | 751, 1298, 1490, 1552, 1691 |
| 32 | H | H | CH$_2$ | —CH$_2$-phenyl | b | 79 | EtOAc/Et$_2$O | |
| 33-34 | H | H | CH$_2$ | allyl | b | 78 | EtOAc/Et$_2$O | 765, 1490, 1565, 1600, 1615, 1685 |
| 35 | H | H | (CH$_2$)$_2$ | allyl | b + d | 53 | EtOH | 755, 1498, 1574, 1615, 1675 |
| 38 | 8-Cl | H | CH$_2$ | —(CH$_2$)$_3$CH$_3$ | b | 70 | EtOAc | 848, 1292, 1494, 1557, 1591, 1612, 1690 |
| 39 | 7-Cl | H | CH$_3$ | —(CH$_2$)$_3$CH$_3$ | a | 69 | EtOAc/Et$_2$O | 815, 1487, 1563, 1605, 1694 |
| 40 | 8-Cl | H | CH$_2$ | —(CH$_2$)$_2$CH$_3$ | a | 75 | EtOAc/Et$_2$O | 850, 1495, 1592, 1613, 1690 |
| 41 | 7-Cl | H | CH$_2$ | —(CH$_2$)$_2$CH$_3$ | a | 71 | EtOAc | 810, 1254, 1490, 1559, 1593 1605, 1685 |
| 42 | 7-Me | H | CH$_2$ | —(CH$_2$)$_3$CH$_3$ | b | 65 | EtOAc | 809, 1503, 1566, 1686 |

STEP B

Using a method similar to that used in Step F of Example 1, and starting from the corresponding compound of formula II, the following compounds of formula I were prepared according to Examples 1-35 and 38-42 as indicated in Table III below.

The product of Example 37 was prepared as indicated below.

A mixture of 1.5 g of 1-chloromethyl-4-methyl[1,2,4]-triazolo[4,3-a]quinazolin-5(4H)-one and 0.7 g of imidazolidinethione in 30 ml of acetone was refluxed for 16 hours and the product crystallized during the reflux. The mixture was filtered and the product washed with acetone and dried under vacuum to obtain 1.95 g (92% yield) of 4-allyl-1-(2chloroethyl)[1,2,4]triazolo[4,3-a]quinazolin-5(4H)-one melting at 245-50 (decomp.)°C. after crystallization from EtOH/Et$_2$O. The product of Example 36 was prepared analogously to Example 37.

Microanalyses of the compounds of formula I prepared in Examples 1 to 42 are given in Table IV.

TABLE III

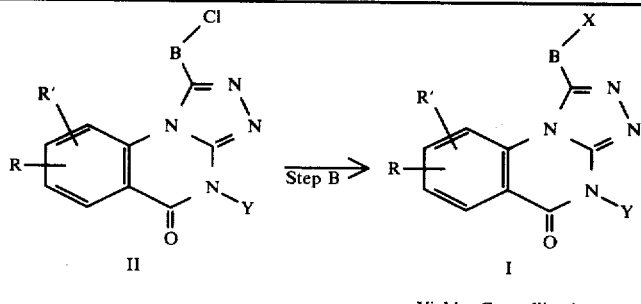

| Ex | R | R' | B | Y | X | Yield % | Crystallization Solvent | IR cm$^{-1}$ |
|---|---|---|---|---|---|---|---|---|
| 1 | H | H | CH$_2$ | —(CH$_2$)$_2$—CH$_3$ | piperidinyl·HCl | 67 | MeOH/Et$_2$O | 761,1503,1587,1623,1696, 2400-2700,3300-3600 |
| 2 | H | H | CH$_2$ | —(CH$_2$)$_2$—CH$_3$ | ° NEt$_2$·HCl | 61 | EtOH/Et$_2$O | 759,1420,1578,1618,1690, |

TABLE III-continued

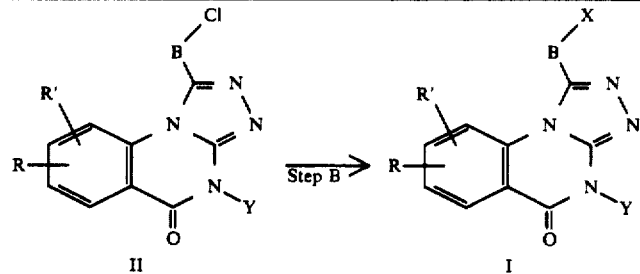

| Ex | R | R' | B | Y | X | Yield % | Crystallization Solvent | IR cm$^{-1}$ |
|----|---|----|----|---|---|---------|------------------------|--------------|
|    |   |    |    |   |   |         |                        | 2200–2600,3300–3600 |
| 3  | H | H  | CH$_2$ | —(CH$_2$)$_2$—CH$_3$ | piperazine-NMe·2HCl | 46 | EtOH/Et$_2$O | 757,1499,1571,1692, 2300–2700,3200–3600 |
| 4  | H | H  | CH$_2$ | —(CH$_2$)$_2$—CH$_3$ | 5-Me-piperidine·HCl | 64 | EtOH/Et$_2$O | 758,1497,1576,1685, 2300–2700,3100–3600 |
| 5  | H | H  | CH$_2$ | —(CH$_2$)$_2$—CH$_3$ | 7-Me-piperidine·HCl | 67 | EtOH/Et$_2$O | 758,1498,1572,1700, 2400–2700,3200–3650 |
| 6  | H | H  | CH$_2$ | —(CH$_2$)$_2$—CH$_3$ | N-Ph-piperazine·HCl | 51 | EtOH/Et$_2$O | 755,1496,1566,1679, 2300–2600,3300–3600 |
| 7  | H | H  | CH$_2$ | —(CH$_2$)$_2$—CH$_3$ | azabicyclic·HCl | 42 | EtOH/Et$_2$O | 756,1496,1572,1699, 2500–2800 |
| 8  | H | H  | CH$_2$ | —(CH$_2$)$_2$—CH$_3$ | 3,5-diMe-piperidine·HCl | 50 | EtOH/Et$_2$O | 757,1070,1512,1620,1663, 1723,2000–2700,3300–3600 |
| 9  | H | H  | CH$_2$ | —(CH$_2$)$_2$CH$_3$ | 2,6-diMe-piperidine·HCl | 20 | EtOH/Et$_2$O | 751,1462,1511,1576,1680, 2000–2500 |
| 10 | H | H  | CH$_2$ | —(CH$_2$)$_2$CH$_3$ | NH nPr·HCl | 74 | EtOH/Et$_2$O | 765,1280,1515,1580,1620, 1670,1730,2360–2840, 3380–3560 |
| 11 | H | H  | CH$_2$ | —(CH$_2$)$_2$CH$_3$ | NH-cyclohexyl·HCl | 79 | EtOH/Et$_2$O | 760,1505,1585,1625,1665, 1705,1730,2400–2900, 3300–3600 |
| 12 | H | H  | CH$_2$ | —(CH$_2$)$_2$CH$_3$ | NH nBu·HCl | 75 | EtOH/Et$_2$O | 760,1505,1580,1605,1625 1702,2500–2850,3320–3600 |
| 13 | H | H  | CH$_2$ | —(CH$_2$)CH$_3$ | N(isoPr)$_2$·HCl | 45 | EtOH/Et$_2$O | 751,1505,1583,1600,1615, 1690,2400–2700,3200–3650 |
| 14 | H | H  | CH$_2$ | —(CH$_2$)$_2$CH$_3$ | N(nBu)$_2$·HCl | 61 | EtOH/Et$_2$O | 760,1505,1575,1605,1625, 1690,2300–2500,3300–3500 |
| 15 | H | H  | CH$_2$ | —(CH$_2$)$_2$CH$_3$ | N(isoBu)$_2$·HCl |    | EtOH/Et$_2$O | 756,1266,1503,1574,1600, |

TABLE III-continued

| Ex | R | R' | B | Y | X | Yield % | Crystallization Solvent | IR cm$^{-1}$ |
|---|---|---|---|---|---|---|---|---|
| | | | | | | | | 1615,1690,2360-2800,3300-3600 |
| 16 | H | H | CH$_2$ | —(CH$_2$)$_2$CH$_3$ | NHCH$_2$CH$_2$—N(piperidine) 2HCl | 79 | EtOH/Et$_2$O | 765,1290,1590,1625,1670, 1695,1725,2500-2800, 3300-3550 |
| 17 | H | H | CH$_2$ | —(CH$_2$)$_2$CH$_3$ | NMe$_2$.HCl | 76 | EtOH/Et$_2$O | 765,1370,1480,1515,1575, 1615,1665,1725 |
| 18 | H | H | CH$_2$ | —(CH$_2$)$_2$CH$_3$ | morpholine 2HCl | 73 | EtOH/Et$_2$O | 760,1075,1515,1610,1645, 1700,2000-2500,3300-3550 |
| 19 | H | H | CH$_2$ | —CH(CH$_3$)$_2$ | piperidine.HCl | 65 | EtOH/Et$_2$O | 760,1285,1460,1500,1570, 1620,1650,1705,2100-2700, 3300-3550 |
| 20 | H | H | CH$_2$ | —CH(CH$_3$)$_2$ | azepane.HCl | 71 | EtOH/Et$_2$O | 765,1295,1420,1495,1575, 1605,1620,1700,2500-2700, 3300-3550 |
| 21 | H | H | CH$_2$ | —(CH$_2$)$_3$CH$_3$ | piperidine | 72 | | 761,1281,1612,1712,2200-2750,3250-3600 |
| 22 | H | H | CH$_2$ | —(CH$_2$)$_3$CH$_3$ | azepane | 60 | EtOH/Et$_2$O | 765,1080,1285,1580,1620, 1655,1720,2200-2700, 3200-3550 |
| 23 | H | H | CH$_2$ | —CH$_3$ | piperidine.HCl | 64 | EtOH/Et$_2$O | 760,1507,1573,1608,1622, 1692,2350-2700,3200-3600 |
| 24 | H | H | CH$_2$ | —CH$_3$ | morpholine.HCl | 73 | EtOH/Et$_2$O | 759,1505,1572,1621,1701, 2350-2700,3200-3600 |
| 25 | H | H | CH$_2$ | —CH$_3$ | piperazine-NCO$_2$Et.2HCl | 70 | EtOH/Et$_2$O | 760,1238,1434,1486,1575, 1618,1690,2100-2500, 3200-3550 |
| 26 | H | H | CH$_2$ | —CH$_3$ | NEt$_2$.HCl | 63 | EtOH/Et$_2$O | 759,1503,1574,1620,1683, 2400-2750,3300-3600 |
| 27 | H | H | CH$_2$ | —CH$_3$ | piperazine-NMe.HCl | 68 | EtOH/Et$_2$O | 760,1506,1618,1676,2350-2750,3200-3600 |

TABLE III-continued

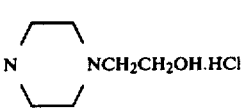

| Ex | R | R' | B | Y | X | Yield % | Crystallization Solvent | IR cm$^{-1}$ |
|---|---|---|---|---|---|---|---|---|
| 28 | H | H | CH$_2$ | —CH$_3$ | piperazine-NCH$_2$CH$_2$OH·HCl | 70 | EtOH/Et$_2$O | 754,1294,1618,1673,1718, 2200-2700,3200-3600 |
| 29 | H | H | CH$_2$ | —C$_2$H$_5$ | piperazine·2HCl | 75 | EtOH/Et$_2$O | |
| 30 | H | H | CH$_2$ | —C$_2$H$_5$ | NEt$_2$ 2HCl | 67 | EtOH/Et$_2$O | |
| 31 | H | H | CH$_2$ | phenyl | piperidine·HCl | 86 | EtOH/Et$_2$O | 760,1500,1556,1698,2400-2700,3200-3600 |
| 32 | H | H | CH$_2$ | —CH$_2$-phenyl | piperidine·HCl | 75 | EtOH/Et$_2$O | 760,1500,1556,1696, 2350-2700,3300-3500 |
| 33 | H | H | CH$_2$ | allyl | piperidine·HCl | 53 | EtOH/Et$_2$O | 757,1271,1490,1574,1600, 1615,1690,2360-2700,2950, 3300-3620 |
| 34 | H | H | CH$_2$ | allyl | azepane·HCl | 79 | EtOH/Et$_2$O | 755,1495,1570,1595,1615, 1690,2500-2750,3300-3600 |
| 35 | H | H | (CH$_2$)$_2$ | allyl | piperidine·HCl | 32 | EtOH/Et$_2$O | 755,1493,1593,1598,1615, 1704,2500-2750,3200-3700 |
| 36 | H | H | CH$_2$ | —CH$_3$ | —S—C(NH$_2$)=NH$_2^+$ Cl$^-$ | 72 | Et$_2$CO | 760,1502,1580,1625,1690, 2600-3550 |
| 37 | H | H | CH$_2$ | —CH$_3$ | —S-imidazolinium Cl$^-$ | 92 | EtOH/Et$_2$O | 760,1500,1576,1596,1621, 1697,2600-3500 |
| 38 | 8-Cl | H | CH$_2$ | —(CH$_2$)$_3$CH$_3$ | piperidine·HCl | 77 | EtOH | 1478,1592,1610,1687,2360-2660br,3340-3600br |

TABLE III-continued

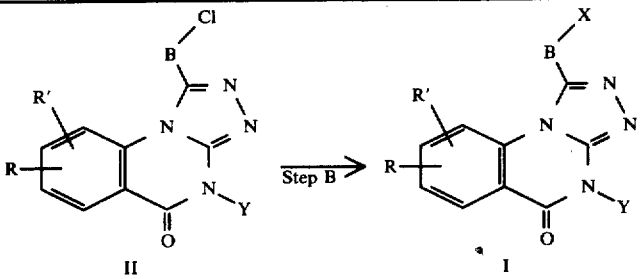

| Ex | R | R' | B | Y | X | Yield % | Crystallization Solvent | IR cm$^{-1}$ |
|---|---|---|---|---|---|---|---|---|
| 39 | 7-Cl | H | CH$_2$ | —(CH$_2$)$_3$CH$_3$ | —N⟨piperidine⟩·HCl | 83 | EtOH/Et$_2$O | 816,1240,1486,1560,1608, 1695,2700–2240br,3660–3330br |
| 40 | 8-Cl | H | CH$_2$ | —(CH$_2$)$_2$CH$_3$ | —N⟨piperidine⟩·HCl | 77 | EtOH | 1475,1590,1610,1683,2360– 2660br,3300–3600br |
| 41 | 7-Cl | H | CH$_2$ | —(CH$_2$)$_2$CH$_3$ | —N⟨piperidine⟩·HCl | 58 | EtOH/Et$_2$O | 815,1484,1570,1598,1610,1690, 2200–2500br,3300–3600br |
| 42 | 7-Me | H | CH$_2$ | —(CH$_2$)$_3$CH$_3$ | —N⟨piperidine⟩·HCl | 61 | EtOH/Et$_2$O | 1418,1603,1654,1711,2200–2750br, 3300–3500br |

TABLE IV

| | | | M.Wt. (incl. H$_2$O) | moles H$_2$O | ANALYSES | | | | | | | |
|---|---|---|---|---|---|---|---|---|---|---|---|---|
| | | | | | CALCULATED | | | | FOUND | | | |
| Examples | M.pt. °C. | Formula | | | % C | % H | % N | % Cl | % C | % H | % N | % Cl |
| 1 | 211–14 | C$_{18}$H$_{24}$N$_5$OCl | 379.9 | 1.0 | 56.91 | 6.90 | 18.43 | 9.93 | 56.90 | 6.90 | 18.62 | 9.63 |
| 2 | 178–82 | C$_{17}$H$_{24}$N$_5$OCl | 358.9 | 0.5 | 56.90 | 7.02 | 19.51 | 9.88 | 56.97 | 6.99 | 19.66 | 10.25 |
| 3 | 225–30 | C$_{18}$H$_{26}$N$_6$OCl$_2$ | 462.9 | 2.75 | 46.71 | 6.86 | 18.16 | 15.32 | 46.76 | 6.84 | 18.33 | 15.43 |
| 4 | 228–32 | C$_{17}$H$_{22}$N$_5$OCl | 365.9 | 1.0 | 55.81 | 6.61 | 19.14 | 9.69 | 55.29 | 6.66 | 18.97 | 9.64 |
| 5 | 196–200 | C$_{19}$H$_{26}$N$_5$OCl | 393.9 | 1.0 | 57.93 | 7.16 | 17.78 | 9.00 | 57.92 | 7.17 | 17.89 | 8.98 |
| 6 | 225–32 | C$_{23}$H$_{27}$N$_6$OCl | 452.5 | 0.75 | 61.06 | 6.35 | 18.57 | 7.83 | 61.03 | 6.54 | 18.26 | 7.54 |
| 7 | 212–6 | C$_{21}$H$_{28}$N$_5$OCl | 401.9 | — | 62.75 | 7.02 | 17.42 | 8.82 | 62.71 | 7.01 | 17.38 | 8.92 |
| 8 | 215–20 | C$_{20}$H$_{28}$N$_5$OCl | | | | | | | | | | |
| 9 | 228–30 | C$_{20}$H$_{28}$N$_5$OCl | | | | | | | | | | |
| 10 | 225–228 | C$_{16}$H$_{22}$N$_5$OCl | 335.8 | — | 57.22 | 6.60 | 20.85 | 10.56 | 57.20 | 6.62 | 20.85 | 10.56 |
| 11 | 210–215 | C$_{19}$H$_{26}$N$_5$OCl | 403.4 | 0.75 | 59.54 | 7.37 | 17.36 | 8.79 | 59.52 | 7.39 | 17.24 | 8.92 |
| 12 | 216–219 | C$_{17}$H$_{24}$N$_5$OCl | 367.9 | 1.0 | 55.50 | 7.12 | 19.04 | 9.64 | 55.21 | 7.09 | 18.88 | 9.55 |
| 13 | 158–163 | C$_{19}$H$_{28}$N$_5$OCl | 377.9 | — | 60.39 | 7.47 | 18.53 | 9.38 | 60.54 | 7.50 | 18.62 | 9.46 |
| 14 | 150–154 | C$_{21}$H$_{32}$N$_5$OCl | | | | | | | | | | |
| 15 | 112–17 | C$_{21}$H$_{32}$N$_5$OCl | 406.0 | — | 62.13 | 7.95 | 17.25 | 8.73 | 61.89 | 7.90 | 17.41 | 8.77 |
| 16 | 141–44 | C$_{20}$H$_{30}$N$_6$OCl$_2$ | 477.4 | 2.0 | 50.31 | 7.18 | 17.60 | | 50.03 | 7.24 | 17.55 | |
| 17 | 203–06 | C$_{15}$H$_{20}$N$_5$OCl | 344.3 | 1.25 | 52.32 | 6.59 | 20.34 | 10.30 | 52.34 | 6.53 | 20.28 | 10.37 |
| 18 | 199–202 | C$_{17}$H$_{23}$N$_5$O$_2$Cl$_2$ | 400.3 | — | 51.01 | 5.79 | 17.49 | 17.71 | 51.03 | 5.84 | 17.42 | 17.36 |
| 19 | 151–154 | C$_{18}$H$_{24}$H$_5$OCl | 379.9 | 1.0 | 56.91 | 6.90 | 18.43 | 9.33 | 57.17 | 6.85 | 18.58 | 9.40 |
| 20 | 144–145.5 | C$_{19}$H$_{26}$N$_5$OCl | 389.4 | 0.75 | 58.60 | 7.12 | 17.98 | 9.10 | 58.51 | 7.21 | 17.41 | 9.39 |
| 21 | 156–156.5 | C$_{19}$H$_{26}$N$_5$OCl | 339.4 | — | 67.23 | 7.42 | 20.63 | | 67.29 | 7.41 | 20.67 | |
| 22 | 122–126 | C$_{20}$H$_{29}$N$_5$OCl$_2$ | 439.9 | 0.75 | 54.61 | 6.99 | 15.92 | 16.12 | 54.68 | 6.89 | 15.94 | 15.72 |
| 23 | 236–40 | C$_{16}$H$_{20}$N$_5$OCl | 338.3 | 0.25 | 56.80 | 6.11 | 20.70 | 10.48 | 56.85 | 6.07 | 20.59 | 10.65 |
| 24 | 225–28 | C$_{15}$H$_{18}$N$_5$O$_2$Cl | 335.8 | — | 53.65 | 5.40 | 20.86 | 10.56 | 53.54 | 5.40 | 20.67 | 10.44 |
| 25 | 175–80 | C$_{18}$H$_{24}$N$_6$O$_3$Cl$_2$ | 461.4 | 1.0 | 46.85 | 5.64 | 18.22 | 15.40 | 46.66 | 5.61 | 18.16 | 15.38 |
| 26 | 210–12 | C$_{15}$H$_{20}$N$_5$OCl | 321.8 | — | 55.99 | 6.22 | 21.77 | 11.04 | 55.76 | 6.28 | 21.54 | 10.94 |
| 27 | 290–92 | C$_{16}$H$_{22}$N$_6$OCl | 366.9 | 1.0 | 52.38 | 6.32 | 22.91 | 9.66 | 52.20 | 6.02 | 22.75 | 9.87 |
| 28 | 301–03 | C$_{17}$H$_{24}$N$_6$O$_2$Cl$_2$ | 396.9 | 1.0 | 51.45 | 6.35 | 21.18 | 8.93 | 51.25 | 6.29 | 21.21 | 9.07 |
| 29 | 180–85 | C$_{17}$H$_{23}$N$_5$OCl$_2$ | 402.3 | 1.0 | 50.76 | 6.26 | 17.41 | 17.63 | 50.97 | 6.12 | 17.35 | 17.53 |
| 30 | 158–60 | C$_{16}$H$_{23}$N$_5$OCl$_2$ | 381.3 | 0.5 | 50.40 | 6.08 | 18.60 | 18.37 | 50.03 | 6.18 | 18.27 | 18.03 |
| 31 | 233–38 | C$_{23}$H$_{28}$N$_5$OCl | 441.0 | Both contain one mole C$_2$H$_5$OH | 62.51 | 6.39 | 15.85 | 8.02 | 62.41 | 6.33 | 15.85 | 8.20 |
| 32 | 223–36 | C$_{24}$H$_{30}$N$_5$OCl | 456.0 | | 63.22 | 6.63 | 15.36 | 7.77 | 63.00 | 6.47 | 15.47 | 7.86 |
| 33 | 208–209 | C$_{18}$H$_{22}$N$_5$OCl | 377.9 | 1.0 | 57.22 | 6.40 | 18.53 | 9.38 | 57.08 | 6.28 | 18.79 | 9.51 |

TABLE IV-continued

| Examples | M.pt. °C | Formula | M.Wt. (incl. $H_2O$) | moles $H_2O$ | CALCULATED % C | % H | % N | % Cl | FOUND % C | % H | % N | % Cl |
|---|---|---|---|---|---|---|---|---|---|---|---|---|
| 34 | 172–74 | $C_{19}H_{24}N_5OCl$ | 391.9 | 1.0 | 58.23 | 6.69 | 17.87 | 9.05 | 58.35 | 6.73 | 18.04 | 9.32 |
| 35 | 228–34 | $C_{19}H_{24}N_5OCl$ | 391.9 | 1.0 | 58.23 | 6.69 | 17.87 | 9.05 | 58.54 | 6.65 | 17.77 | 9.14 |
| 36 | 227–30 | $C_{12}H_{13}N_6SOCl$ | 324.8 | 1.0 | 42.04 | 4.38 | 24.53 | 10.36 | 42.43 | 4.29 | 24.61 | 10.44 |
| 37 | 245–50 | $C_{14}H_{15}N_6OSCl$ | 377.9 | 1.5 | 44.50 | 4.80 | 22.24 | 9.38 | 44.71 | 4.51 | 22.23 | 9.38 |
| 38 | 188–95 | $C_{19}H_{25}N_5OCl_2$ | 410.4 |  | 55.61 | 6.14 | 17.07 | 17.28 | 55.74 | 6.10 | 17.27 | 17.21 |
| 39 | 193–200 | $C_{19}H_{25}N_5OCl_2$ | 410.4 |  | 55.61 | 6.14 | 17.07 | 17.28 | 55.58 | 6.10 | 17.23 | 17.49 |
| 40 | 281–87 | $C_{18}H_{23}N_5OCl_2$ | 414.1 | 1.0 | 52.18 | 6.09 | 16.90 | 17.11 | 52.26 | 6.04 | 17.12 | 17.19 |
| 41 | 200–01 | $C_{18}H_{25}N_5OCl_2$ | 396.3 |  | 54.55 | 5.85 | 17.67 | 17.89 | 54.60 | 5.84 | 17.79 | 17.90 |
| 42 | 227–29 | $C_{20}H_{29}N_5OCl_2$ | 444.4 | 1.0 | 54.05 | 7.03 | 15.75 | 15.96 | 54.05 | 6.89 | 15.83 | 15.90 |

EXAMPLE 43

1-piperidinomethyl-4-n-propyl[1,2,4]triazolo[4,3-a]quinazolin-5(4H)-one hydrochloride monohydrate 5.0 g of 4-allyl-1-piperidinomethyl[1,2,4]triazolo[4,3-a]quinazolin-5(4H)-one, prepared as described in Example 33, were suspended in 300 ml of a 1-1 chloroform-ethanol mixture and 500 mg of 5% palladized carbon were added thereto. The resultant mixture was hydrogenated at room temperature for 1.5 hours until the calculated amount of hydrogen had been absorbed and the mixture was filtered. The filtrate was evaporated to dryness to obtain 4.3 g of the free base as a colorless solid. The free base was converted into the hydrochloride salt, monohydrate analagously to Example 1. The product thus obtained was identical with respect to melting point, IR and NMR to the product obtained in Example 1.

EXAMPLE 44

Tablets were prepared according to the formulation:

| Product of Example 1 | 15 mg |
|---|---|
| excipient q.s. for one tablet up to | 100 mg |

(Details of the excipient: lactose, starch, talc, magnesium stearate).

EXAMPLE 45

A dosed aerosol was prepared delivering per dose:

| Product of Example 1 | 2 mg |
|---|---|
| emulsifier | 0.15 mg |
| propellant | 50 mg |

EXAMPLE 46

A syrup was prepared according to formulation:

| Product of Example 1 | 0.3 g |
|---|---|
| odoring and sweetening excipient q.s.p. | 100 ml |

PHARMACOLOGICAL STUDY (A) Effects on histamine-induced bronchoconstriction in anaesthetised guinea pigs (KRG)

Male Dunkin Hartley guinea-pigs weighing 350–650 grams were anaesthetised with urethane (25% w/v solution in distilled water at 7.0 ml/kg i.p). The preparation was described by Konsett and Rossler (1940). The animals were ventilated with a ventilatory pump, stroke volume of 8 ml and frequency of 52 to maintain a lung inflation pressure of 10 cm of $H_2O$. Blood pressure was measured via a cannula in the right carotid artery connected to a Statham blood pressure transducer and a Devices $M_2$ recorder. The test compounds were administered via the cannulated left jugular vein and washed in with 0.1 ml of 0.9% w/w NaCl in distilled water. The test product was administered immediately before the histamine which was used as the agonist.

Respiratory changes were recorded via a differential transducer connected to an SE 905 transducer/converter which in turn was connected to a Devices $M_2$ recorder.

Ref. Konzett, H. and Rossler, R. (1940) Arch. exp. Path. Pharmakol. 1195 71.

The results given in Table V show the effective dose of each of the test compounds required to reduce the histamine-induced constriction in lung air volume by 50%.

(B) Measurement of Pulmonary Compliance and Resistance (RMG)

Male Dunkin Hartley guinea-pigs weighing between 400 and 650 g were anaesthetised with a combination of Hypnorm (1 ml/kg i.m.) and Valium (5 mg/kg i.p.). The trachea was cannulated and cannulae were inserted into the right jugular vein for the administration of compounds and left carotid artery for blood pressure measurement.

The animals were ventilated at a tidal volume of 6–8 ml and 10–12 $cmH_2O$ distension pressure was obtained. The respiratory rate was adjusted to 40–50/min. The animals were pre-treated with gallamine triethiodide (4 mg/kg i.v.) to maintain paralysis of respiratory muscles. Oxygen enrichment was applied to the inspiratory limb of the ventilator.

Respiratory resistance was measured by forced oscillation (Clay and Hughes 1980). Sinusodal wave forms of pressure were divided by flow at constant lung volumes to detect resistance changes. Sine wave production was achieved by a loudspeaker driven at 6–7 Hz through a pressure transducer, pneumotachograph and differential pressure transducer to detect pressure and flow contributions of the wave form. Instantaneous analysis of the resistance was achieved with an analogue device and charted onto a Device M4 recorder. Drugs and analysis of activity were as described for the Konzett Rossler technique. Ref. Clay, T. P. and Hughes, J. M. B. (1980) J. Physiol. 308 427–437. The results given in Table V show the effective dose of each of the test compounds required to reduce the histamine induced resistance change by 50%.

TABLE V

| Product of Example | KRG ED$_{50}$ (mg/Kg) | RMG ED$_{50}$ (mg/kg) |
|---|---|---|
| 1 | 0.12 | |
| 2 | | 0.50 |
| 3 | 5.28 | |
| 4 | 2.0 | |
| 5 | 0.096 | 0.3 |
| 6 | 5.0 | |
| 7 | 0.33 | |
| 8 | 1.0 | |
| 10 | 1.97 | |
| 11 | 1.8 | |
| 12 | 1.3 | |
| 14 | 2.9 | |
| 19 | 0.185 | |
| 20 | 0.8 | |
| 21 | 0.11 | 0.15 |
| 22 | 0.84 | |
| 23 | >1 | 1.0 |
| 24 | 2.76 | 1.8 |
| 25 | 5.0 | 3.5 |
| 26 | 3.75 | 1.0 |
| 27 | | 0.8 |
| 29 | 0.35 | 0.5 |
| 30 | | 1.0 |
| 31 | 0.58 | |
| 33 | 0.31 | |

Various modifications of the compounds and methods of the invention may be made without departing from the spirit or scope thereof and it should be understood that the invention is intended to be limited only as defined in the appended claims.

What we claim is:

1. A compound selected from the group consisting of triazoloquinazolones of the formula

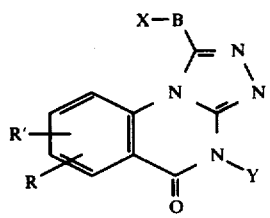

wherein R and R' are individually selected from the group consisting of hydrogen, halogen, nitro and alkyl and alkoxy of 1 to 3 carbon atoms, Y is selected from the group consisting of alkyl of 1 to 6 carbon atoms, alkenyl of 2 to 4 carbon atoms, cycloalkyl of 3 to 8 carbon atoms, aryl of 6 to 8 carbon atoms and aralkyl of 7 to 8 carbon atoms, B is an alkylene of 1 to 3 carbon atoms, X is selected from the group consisting of

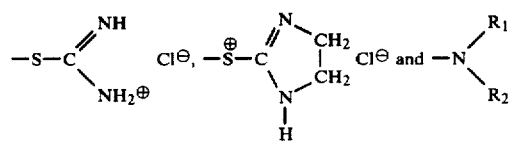

$R_1$ and $R_2$ are individually selected from the group consisting of hydrogen, alkyl of 1 to 6 carbon atoms, cycloalkyl of 3 to 8 carbon atoms, aryl of 6 to 8 carbon atoms, aralkyl of 7 to 8 carbon atoms, aminoalkyl of 2 to 4 carbon atoms, mono- and dialkylaminoalkyl with each alkyl having 2 to 4 carbon atoms, piperidinoalkyl of 1 to 4 alkyl carbon atoms, morpholinoalkyl of 1 to 4 alkyl carbon atom and piperazinylalkyl of 1 to 4 alkyl carbon atoms or $R_1$ and $R_2$ taken together with the nitrogen to which they are attached form a saturated mono- or bicyclic heterocyclic ring selected from the group consisting of pyrrolidinyl, piperidino, 2,3,4,5,6,7-hexahydro-azepino, 3-azabicyclo[3,2,2,]nonano, 2,6-dimethyl-piperidino, 3,5-dimethylpiperidino, morpholino, thiomorpholine and piperazin-1-yl and their non-toxic, pharmaceutically acceptable acid addition salts.

2. A compound of claim 1 wherein R and R' are individually selected from the group consisting of hydrogen, chlorine, nitro, methyl and methoxy, Y is selected from the group consisting of alkyl of 1 to 6 carbon atoms, cyclohexyl, allyl, phenyl and benzyl and B is methylene or ethylene.

3. A compound of claim 2 wherein R and R' are hydrogen Y is selected from the group consisting of methyl, ethyl, n-propyl, isopropyl, n-butyl, tert.-butyl, n-hexyl, cyclohexyl, allyl, phenyl and benzyl and X is selected from the group consisting of amino, dimethylamino, diethylamino, dipropylamino, diisopropylamino, dibutylamino, diisobutylamino, butylamino, cyclohexylamino, piperidinoethylamino, pyrrolidinyl, piperidino, 2,3,4,5,6,7-hexahydroazepino, 3-azabicyclo[3,2,2-]nonano, 2,6-dimethylpiperidino, 3,5-dimethylpiperidino, morpholino, piperazin-1-yl, methylpiperazin-1-yl, hydroxyethylpiperazin-1-yl, phenylpiperazin-1-yl and ethoxycarbonylpiperaziny-1-yl.

4. A compound of claim 3 wherein B is —CH$_2$— and X is selected from the group consisting of pyrrolidinyl, piperidino, 2,3,4,5,6,7-hexahydroazepino, 3-azabicyclo[3,2,2]nonano, 2,6-dimethylpiperidino and 3,5-dimethylpiperidino.

5. A compound of claim 1 selected from the group consisting of
- 1-piperidinomethyl-4-ethyl[1,2,4]triazolo[4,3-a]quinazolin-5(4H)-one;
- 1-piperidinomethyl-4-n-propyl[1,2,4]triazolo[4,3-a]quinazolin-5(4H)-one;
- 1-piperidinomethyl-4-isopropyl[1,2,4]triazolo[4,3-a]quinazolin-5(4H)-one;
- 1-piperidinomethyl-4-n-butyl[1,2,4]triazolo[4,3-a]quinazolin-5(4H)-one;
- 1-(2,3,4,5,6,7-hexahydroazepino)methyl-4-n-butyl[1,2,4]triazolo[4,3,-a]quinazolin-5(4H)-one;
- 1-piperidinomethyl-4-allyl[1,2,4]triazolo[4,3-a]quinazolin-5(4H)-one and their non-toxic, pharmaceutically acceptable acid addition salts.

6. An antihistaminic and bronchospasmolytical composition comprising and antihistaminically and bronchospasmolytically effective amount of at least one compound of claim 1 and a pharmaceutical carrier.

7. A composition of claim 6 wherein R and R' are individually selected from the group consisting of hydrogen, chlorine, nitro, methyl and methoxy, Y is selected from the group consisting of alkyl of 1 to 6 carbon atoms, cyclohexyl, allyl, phenyl and benzyl and B is methylene or ethylene.

8. A composition of claim 7 wherein R and R' are hydrogen, Y is selected from the group consisting of methyl, ethyl, n-propyl, isopropyl, n-butyl, tert.-butyl, n-hexyl, cyclohexyl, allyl, phenyl and benzyl and X is selected from the group consisting of amino, dimethylamino, diethylamino, dipropylamino, diisopropylamino, dibutylamino, diisobutylamino, butylamino, cyclohexylamino, piperidinoethylamino, pyrrolidinyl, piperidino, 2,3,4,5,6,7-hexahydroazepino, 3-azabicyclo[3,2,2-]nonano, 2,6-dimethylpiperidino, 3,5-dimethylpiperidino, morpholino, piperazin-1-yl, methylpiperazin-1-yl, hydroxyethylpiperazin-1-yl, phenylpiperazin-1-yl and ethoxycarbonylpiperazin-1-yl.

9. A composition of claim 8 wherein B is —CH$_2$— and X is selected from the group consisting of pyrrolidinyl, piperidino, 2,3,4,5,6,7-hexahydroazepino, 3-azabicyclo[3,2,2]nonano, 2,6-dimethylpiperidino and 3,5-dimethylpiperidino.

10. A composition of claim 6 wherein the active compound is selected from the group consisting of 1-piperidinomethyl-4-ethyl[1,2,4]triazolo[4,3-a]quinazolin-5(4H)-one;
1-piperidinomethyl-4-n-propyl[1,2,4]triazolo[4,3-a]quinoazolin-5(4H)-one;
1-piperidinomethyl-4-isopropyl[1,2,4]triazolo[4,3-a]quinazolin-5(4H)-one;
1-piperidinomethyl-4-n-butyl[1,2,4]triazolo[4,3-a]quinazolin-5(4H)-one;
1-(2,3,4,5,6,7-hexahydroazepino)methyl-4-n-butyl[1,2,4]triazolo[4,3-a]quinazolin-5(4H)-one;
1-piperidinomethyl-4-allyl[1,2,4]triazolo[4,3-a]quinazolin-5(4H)-one and their non-toxic, pharmaceutically acceptable acid addition salts.

11. A method of inducing antihistaminic and bronchospasmolytic activity in warm-blooded animals comprising administering to warm-blooded animals an antihistaminically and bronchospasmolytically effective amount of at least one compound of claim 1.

12. The method of claim 11 wherein R and R' are individually selected from the group consisting of hydrogen, chlorine, nitro, methyl and methoxy, Y is selected from the group consisting of alkyl of 1 to 6 carbon atoms, cyclohexyl, allyl, phenyl and benzyl and B is methylene or ethylene.

13. The method of claim 12 wherein R and R' are hydrogen, Y is selected from the group consisting of methyl, ethyl, n-propyl, isopropyl, n-butyl, tert.-butyl, n-hexyl, cyclohexyl, allyl, phenyl and benzyl and X is selected from the group consisting of amino, dimethylamino, diethylamino, dipropylamino, diisopropylamino, dibutylamino, diisobutylamino, butylamino, cyclohexylamino, piperidinoethylamino, pyrrolidinyl, piperidino, 2,3,4,5,6,7-hexahydroazepino 3-azabicyclo[3,2,2]nonano, 2,6-dimethylpiperidino, 3,5-dimethylpiperidino, morpholino, piperazin-1-yl, methylpiperazin-1-yl, hydroxyethyl, piperazin-1-yl, phenylpiperazin-1-yl and ethoxycarbonylpiperazin-1-yl.

14. The method of claim 13 wherein B is —CH$_2$— and X is selected from the group consisting of pyrrolidinyl, piperidino, 2,3,4,5,6,7-hexahydroazepino, 3-azabicyclo[3,2,2]nonano, 2,6-dimethylpiperidino and 3,5-dimethylpiperidino.

15. The method of claim 11 wherein the active compound is selected from the group consisting of 1-piperidinomethyl-4-ethyl[1,2,4]triazolo[4,3-a]quinazolin-5(4H)-one;
1-piperidinomethyl-4-n-propyl[1,2,4]triazolo [4,3-a]quinazolin-5(4H)-one;
1-piperidinomethyl-4-isopropyl[1,2,4]triazolo[4,3-a]quinazolin-5(4H)-one;
1-piperidinomethyl-4-n-butyl[1,2,4]triazolo[4,3-a]quinazolin-5(4H)-one;
1-(2,3,4,5,6,7-hexahydroazepino)methyl-4-n-butyl[1,2,4]triazolo[4,3-a]quinazolin-5-(4H)-one;
1-piperidinomethyl-4-allyl[1,2,4]triazolo[4,3-a]quinazolin-5(4H)-one and their non-toxic, pharmaceutically acceptable acid addition salts.

16. A compound of the formula

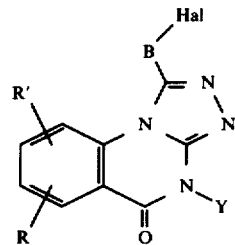

wherein R, R', Y and B are as defined in claim 1 and Hal is chlorine or bromine.

* * * * *